United States Patent
Lavergne

(10) Patent No.: US 8,146,428 B2
(45) Date of Patent: Apr. 3, 2012

(54) SAFETY SYSTEM

(76) Inventor: Terry J. Lavergne, Lafayette, LA (US)

(*) Notice: Subject to any disclaimer, the term of this patent is extended or adjusted under 35 U.S.C. 154(b) by 385 days.

(21) Appl. No.: 12/462,752

(22) Filed: Aug. 7, 2009

(65) Prior Publication Data

US 2010/0037710 A1 Feb. 18, 2010

Related U.S. Application Data

(60) Provisional application No. 61/188,435, filed on Aug. 8, 2008.

(51) Int. Cl.
*G01H 1/00* (2006.01)
(52) U.S. Cl. ........................................ 73/583
(58) Field of Classification Search .................. 73/583; 200/83 R
See application file for complete search history.

(56) References Cited

U.S. PATENT DOCUMENTS

| | | | | |
|---|---|---|---|---|
| 4,894,497 A * | 1/1990 | Lycan | 200/83 R |
| 4,977,418 A * | 12/1990 | Canty | 396/19 |
| 5,192,194 A * | 3/1993 | Birdwell | 417/9 |
| 5,257,639 A * | 11/1993 | Prescott et al. | 137/82 |
| 5,422,494 A * | 6/1995 | West et al. | 250/551 |
| 5,425,279 A * | 6/1995 | Clark et al. | 73/865.8 |
| 5,604,532 A * | 2/1997 | Tillmanns | 348/84 |
| 6,707,195 B1 * | 3/2004 | De Martino | 310/88 |
| 7,351,926 B2 * | 4/2008 | Hillman | 200/81 R |

* cited by examiner

*Primary Examiner* — Lisa Caputo
*Assistant Examiner* — Octavia Davis-Hollington
(74) *Attorney, Agent, or Firm* — Jacobson and Johnson; Thomas N. Phung

(57) ABSTRACT

A safety system for testing high-pressure devices comprising an explosion-proof safety housing; a high-pressure pneumatics testing equipment located within the housing; a closeable access opening in the housing for inserting a high-pressure device for testing within the housing; a device located within the housing for coupling the high-pressure pneumatics testing equipment to the high-pressure device for testing; a control panel located outside the housing; and a device linking the high-pressure pneumatics testing equipment to the control panel for operating the high-pressure pneumatics testing equipment within the safety housing from the control panel.

19 Claims, 5 Drawing Sheets

TEST BUNKER

SAFETY SYSTEM

CROSS REFERENCE TO RELATED APPLICATIONS

This application claims priority to U.S. Provisional Application Ser. No. 61/188,435; filed on Aug. 8, 2008; titled IMPROVED SAFETY SYSTEM.

STATEMENT REGARDING FEDERALLY SPONSORED RESEARCH OR DEVELOPMENT

None

REFERENCE TO A MICROFICHE APPENDIX

None

FIELD OF THE INVENTION

This invention relates generally to safety systems and more specifically to an improved safety system for safely testing of high-pressure devices and the various components of the high-pressure devices.

BACKGROUND OF THE INVENTION

The testing of high-pressure devices and the various components of the high-pressure devices, by its very nature, is an inherently dangerous activity as one is in search of faults in devices that can potentially lead to disastrous. Although safety equipments such as check valves, rupture disks and relief valves have been incorporated to the high-pressure devices to minimize risk, not amount safety equipments can be incorporate to eliminate all, especially the potentially fatal ones. Examples of two types of hazards that are associated with the testing of high-pressure devices include shock from a pressure blast and flying fragments and debris. In regards to shock from a pressure blast, it has been found that more than half the energy released by an explosion is radiated outward by the shock wave. Low shock pressures in the range of 2 to 15 psi overpressures may be sufficient to damage most man-made structures. The energy released to create such overpressures may result from combustion, or may be due to the release of elastic energy stored in a compressible fluid.

In regards to the hazard of flying fragments and debris, flying fragments and debris hazard is always present in all types of high pressure. The safety issue with regards to flying fragments and debris centers around the protection of personnel and equipment from damage due to the flying fragments and debris in the event of an explosion.

The main problems design problems associated with the hazards of shock from a pressure blast and flying fragments and debris is the creation of high-pressure testing equipments that will operate safely under the desired pressure and the creation of a barrier that will not only stop the fragments in case the high-pressure testing equipment happens to fail but will also include safety features to help minimize the exposure of operator(s) to the high-pressure testing equipment during the testing stage.

SUMMARY OF THE INVENTION

The present invention comprises a safety system for testing high-pressure devices comprising an explosion-proof safety housing having high-pressure pneumatics testing equipment located within the safety housing. The safety housing includes a closeable access opening in the safety housing for inserting a high-pressure device for testing within the safety housing. The safety system includes means within the safety housing for coupling the high-pressure pneumatics testing equipment to the high-pressure device for testing. The safety system also includes a control panel located outside of the safety housing and means linking the high-pressure pneumatics testing equipment to the control panel for operating the high-pressure pneumatics testing equipment within the safety housing from the control panel.

The present invention also includes a method for safely testing high-pressure devices including the steps of providing an explosion-proof safety housing; placing high-pressure pneumatics testing equipment within the housing; forming a closeable access opening in the housing; inserting a high-pressure device for testing within the housing through the access opening; providing a control panel outside the housing; coupling the control panel to the testing equipment inside the housing; and then operating said high-pressure pneumatics testing equipment from the control panel for testing high-pressure devices.

DESCRIPTION OF THE PREFERRED EMBODIMENT

Figure 1:
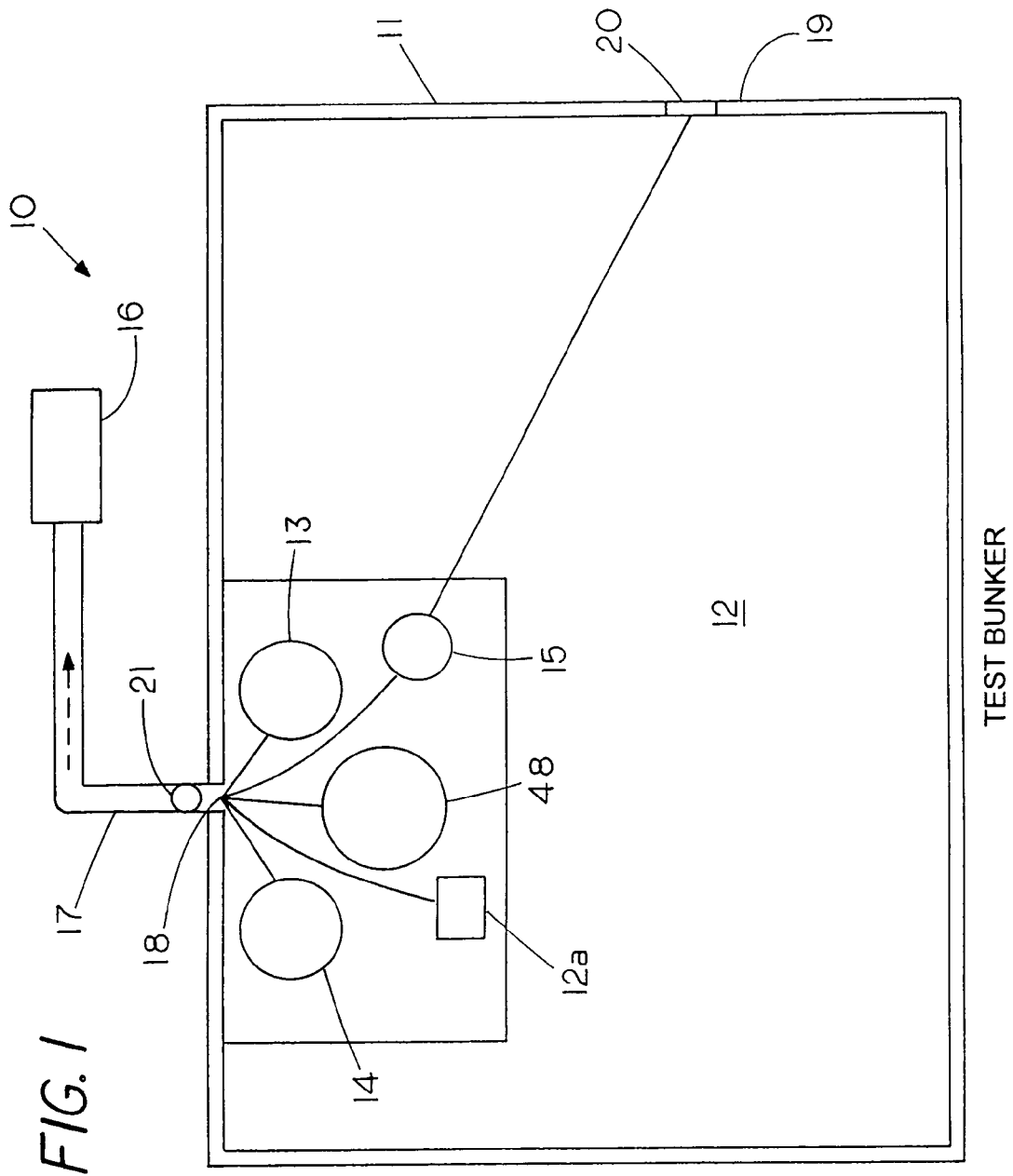
FIG. 1 shows a schematic view of an embodiment of a safety system.

FIG. 1 shows a schematic view of an embodiment of a safety system 10 of the present invention for safely pressure testing high-pressure devices and components of high-pressure equipments with various fluids including air, nitrogen dioxide water and various types of oils. Some of the devices to be tested include but are not limited to transfer pipes, well heads, various types of downhole tool, blowout preventers or BOPs including ram BOPs and annular BOPs. The devices may either be new or remanufactured.

Safety system 10 includes a stationary explosion-proof safety housing comprising a bunker housing 11 having a chamber 12 therein. In regards to bunker housing 11, bunker housing 11 may be form from a plurality of materials that is able to withstand the impact of high velocity projectile/high-speed flying fragments resulting from explosion of pressure equipments including valves, piping, fittings, ruptured disks, intensifiers and pumps, as well as pressure vessels. The materials of bunker housing 11 may also be able to withstand and confine shock wave or shock pressure radiated by explosions resulting from the use of a gas as the pressure medium in high-pressure testing or is fluids is used as the pressure medium in high-pressure testing, the flashing or geysering of a compressed fluid to a vapor state resulting from the compressed fluid rapidly passing through an orifice wherein elastic energy is then converted to heat. Suitable materials for the manufacture of bunker housing 11 include but are not limited to concrete and various metals such as steel, aluminum and their alloys.

Located entirely within chamber 12 is at least one high-pressure pneumatics testing equipment and means 12a for coupling the high-pressure pneumatics testing equipment to a high-pressure device for testing. Safety system 10 also includes a closeable access opening comprising a door 19 in bunker housing 11 for inserting a high-pressure device for testing within bunker housing 11. It should be noted that the number of high-pressure equipment testing equipment supported in chamber 12 may varying from as few as one to a plurality of devices and types of high-pressure equipment testing equipments may all be the same, all different or a combination thereof.

The high-pressure equipment testing equipments may be fluid driven and are controlled by pneumatic switches located outside of bunker housing 11 for safety purposes so as to keep all pressure in the bunker housing 11 away from the operator. In the embodiment of FIG. 1, the high-pressure equipment testing equipments are shown as comprising a low-pressure pump 13, an intermediate-pressure pump 14, and a high-pressure pump 48 to provide sequential increase in the pressure to the high-pressure devices being tested. Example of possible pressure ranges would be the low-pressure pump 13 providing up to 4,000 psi (pounds per square inch), the intermediate-pressure pump 14 providing up to 20,000 psi, and the high-pressure pump 48 providing up to 150,000 psi.

Safety system 10 also includes a control panel 16 located outside of the chamber 12 of bunker housing 11 and means linking the high-pressure pneumatics testing equipment to the control panel 16 for operating the high-pressure pneumatics testing equipment within bunker housing 11 from control panel 16. In general the means linking the high-pressure pneumatics testing equipment to control panel 16 includes not only means for monitoring but also recording the operation of the high-pressure pneumatics testing equipment.

By calling for the high-pressure equipment testing equipment(s) to be entirely located within chamber 12, a majority if not all associated pumps, plumbing, hoses, and bleed valves are to also be located entirely within chamber 12. The high-pressure pneumatics testing equipment(s) however are operable outside or remote from chamber 12 and controlled by the control panel 16.

In the embodiment of FIG. 1, the safety system 10 also includes a bleed valve 15 that is located also within chamber 12 and coupled to the high-pressure testing equipment and a sensor comprising a safety enter switch 20 for sensing that the door 19 is closed. Safety enter switch 20 is coupled to bleed valve 15 and functions to activate bleed valve 15 to prevent pressure buildup in the high-pressure testing equipment if the access opening is not closed. In the embodiment of FIG. 1, safety enter switch 20 is shown is shown located at the door 19.

In operation, bleed valve 15 is spring-loaded to initially maintain bleed valve 15 in an opened condition to preventing pressure build-up in the high-pressure pneumatics testing equipment. When safety enter switch 20 senses that door 19 is closed, housing door 19 is locked with a device such as an air cylinder so that no user/personnel can enter chamber 12. The locking of housing door 19 introduces an air flow into bleed valve 15 to actuate bleed valve 15 to a closed condition to allow pressure build-up in the high-pressure pneumatics testing equipment located in chamber 12. However, if the housing door 19 is not closed, the bleed valve 15 will be prevented from closing so that pressure cannot be built up in any of the components located in chamber 12. In addition, if safety enter switch 20 is somehow tampered with, the safety enter switch 20 will prevent air flow to bleed valve 15 thus causing bleed valve 15 to either be maintained or return to the opened condition so that all pressure of safety system 10 will bleed off. The aforementioned safety features will help to prevent the user from being in the vicinity of any pressurized tool(s) in chamber 12.

Although the low-pressure pump 13, intermediate-pressure pump 14, high-pressure pump 48, and the bleed valve 15 may be linked to the control panel 16 by a variety of means, the embodiment of FIG. 1 shows the control panel 16 linked to the low-pressure pump 13, intermediate-pressure pump 14, high-pressure pump 47, and the bleed valve 15 by a ⅛" 60,000 psi rate cone and reinforced thread tubing 17 with a 4 to 1 safety factor. Tubing 17 runs from the chamber 12 through a small opening 18 on bunker housing 11 to the control panel 16 and may also be reinforce by a steel piping.

Although not required, as a safety precaution, the embodiment of FIG. 1 also includes a 3-way pneumatic piloted valve 21 located on tubing 17 between the high-pressure equipment testing equipments (low-pressure pump 13, intermediate-pressure pump 14, high-pressure pump 47, and the bleed valve 15) and control panel 16. 3-way pneumatic piloted valve 21 may be locate either inside chamber 12 or outside of bunker housing 11 and function to turn the high-pressure equipment testing equipments on and off by various switches, such as switches located and/or controlled by the control panel 16. Use of the 3-way pneumatic piloted valve 21 permits air in the high-pressure equipment testing equipments and associated tubing in chamber 12 to bleed off instantly. In view of the above, safety system is typically considered as a pneumatically controlled system.

Figure 2:
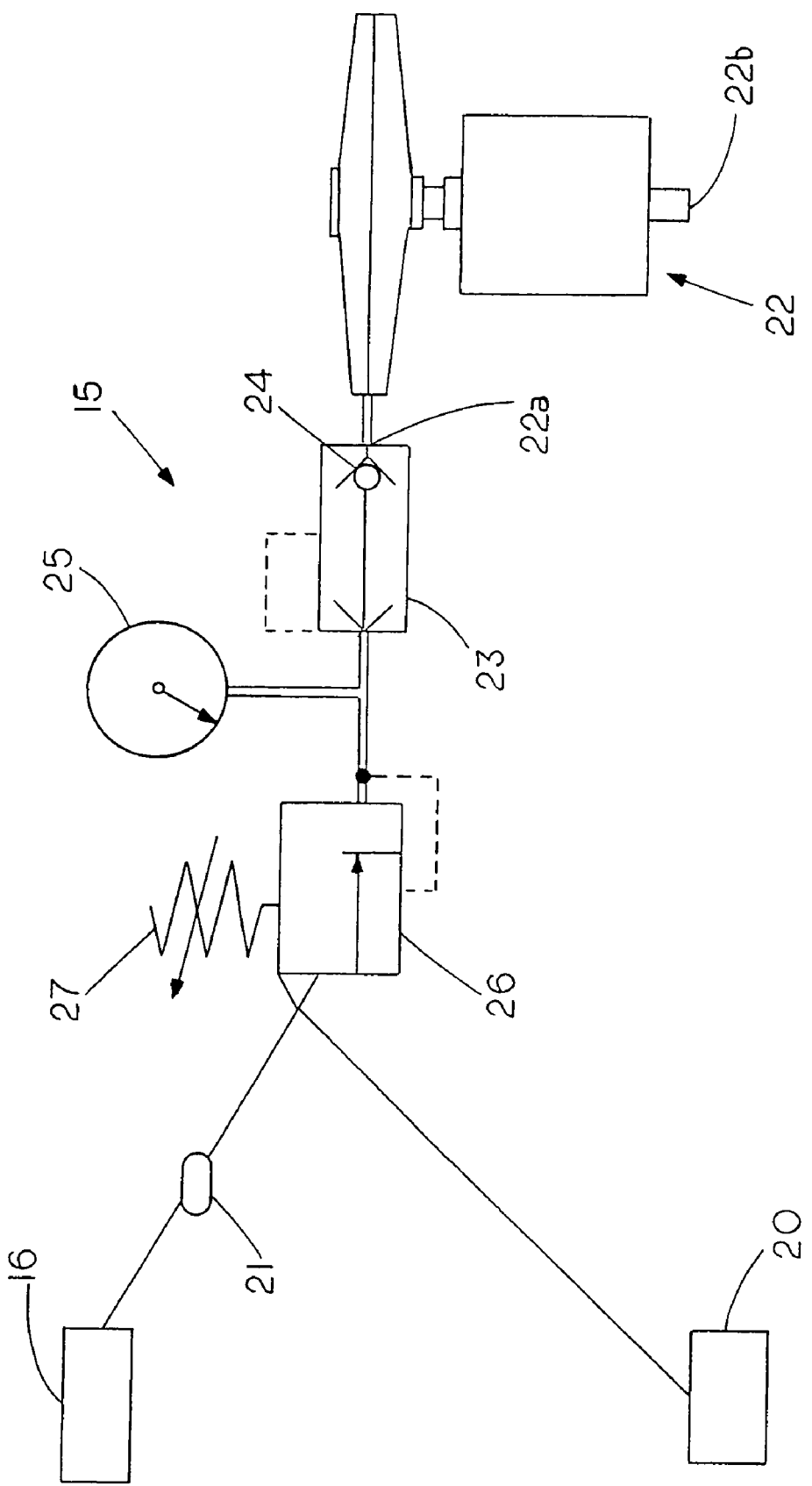
FIG. 2 shows a schematic view of the general components of the bleed valve.

FIG. 2 shows a schematic view of an example of the general components of the bleed valve 15 of safety system 10 comprising a bleed valve body 22, a quick exhaust 23, an air drive pressure gauge 25, and an air regulator 26. Bleed valve body 22 is shown as having an inlet 22a and an outlet 22b with quick exhaust 23 connected to bleed valve 22 at inlet 22a. Quick exhaust 23 functions to help rapidly exhaust air out of the bleed valve 22 into bunker housing 11. Quick exhaust 23 is in fluid communication with air regulator 26 and includes a ball valve 24 supported therein to control the flow of air into bleed valve body 22. Air drive pressure gauge 25 functions to display the pressure in bleed valve 15, such as in pressure per square inch (psi), and is positioned between and in fluid communication with both quick exhaust 23 and air regulator 26.

In regards to air regulator 26, air regulator 26 connects control panel 16 and safety enter switch 20 to bleed valve 15 and includes an adjustable resistor 27 to allow the user to control the amount fluid flow that is directed into bleed valve 15. For example, in the present embodiment adjustable resistor 27 is set so as to allow air regulator 26 to support a fluid flow at levels around 80 psi.

Figure 3:
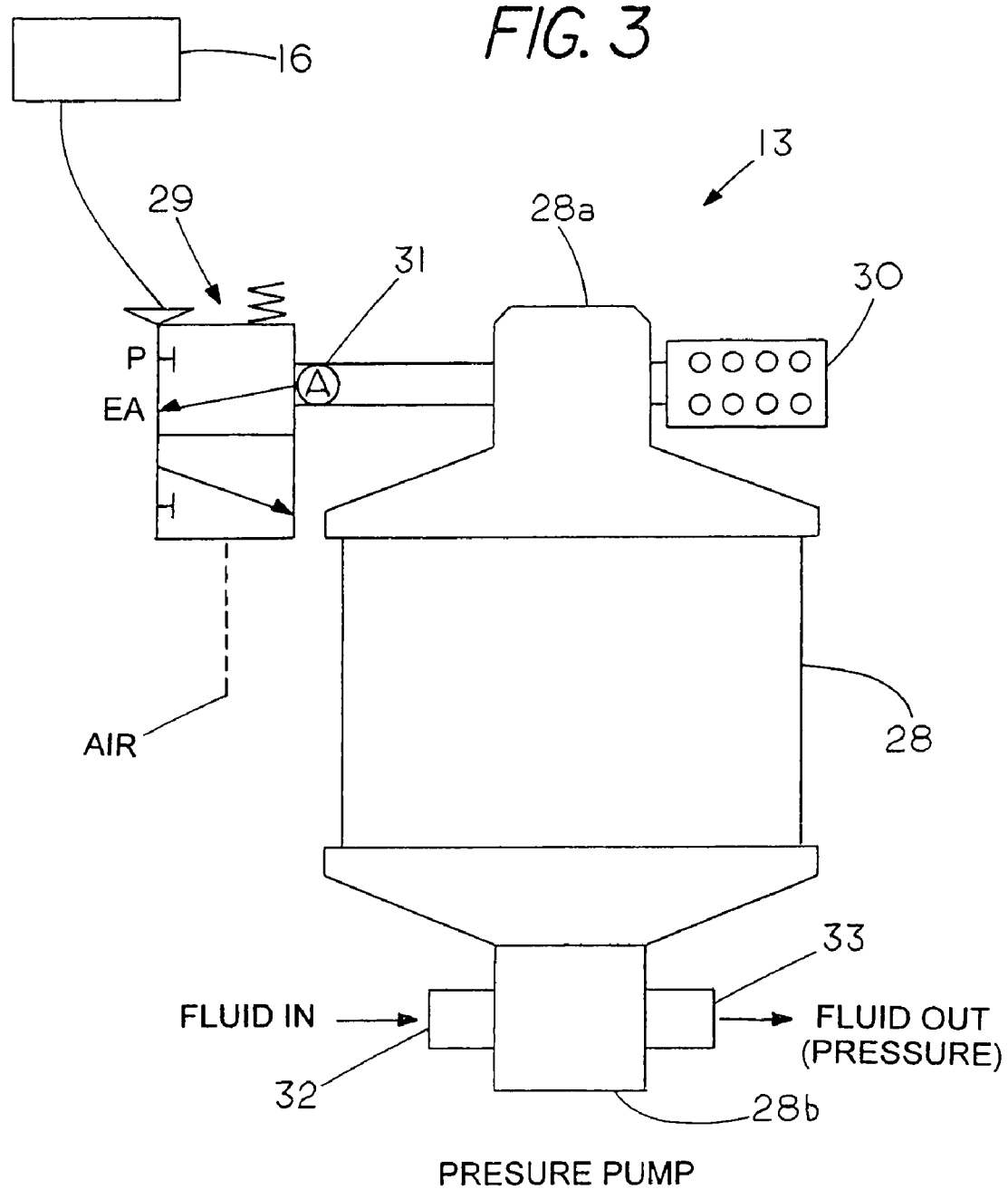
FIG. 3 shows a schematic view of the general components of the pressure pump.

FIG. 3 shows a schematic view of the general components of the low-pressure pump 13 of safety system 10 comprising a pressure pump body 28 having a first end 28a and a second end 28b. The first end 28a of pressure pump body 28 is located between and in fluid communication with a pump on/off valve 29 and an exhaust 30. Located between pump on/off valve 29 and first end 28a of pressure pump body 28 is a 3-way pneumatic valve 31. As shown in FIG. 3, pump on/off valve 29 is connected to control panel 16 and is air operated to switch pump on/off valve 29 on and off. Although not required, a further safety feature of the present embodiment is that in order to maintain pump on/off valve 29 in an on condition, the user/operator must manually and continuously engage the control switch located on control panel 16.

Located proximal the second end 28a of pressure pump body 28 is a pressure pump fluid inlet 32 and a pressure pump fluid outlet 33.

Figure 4:
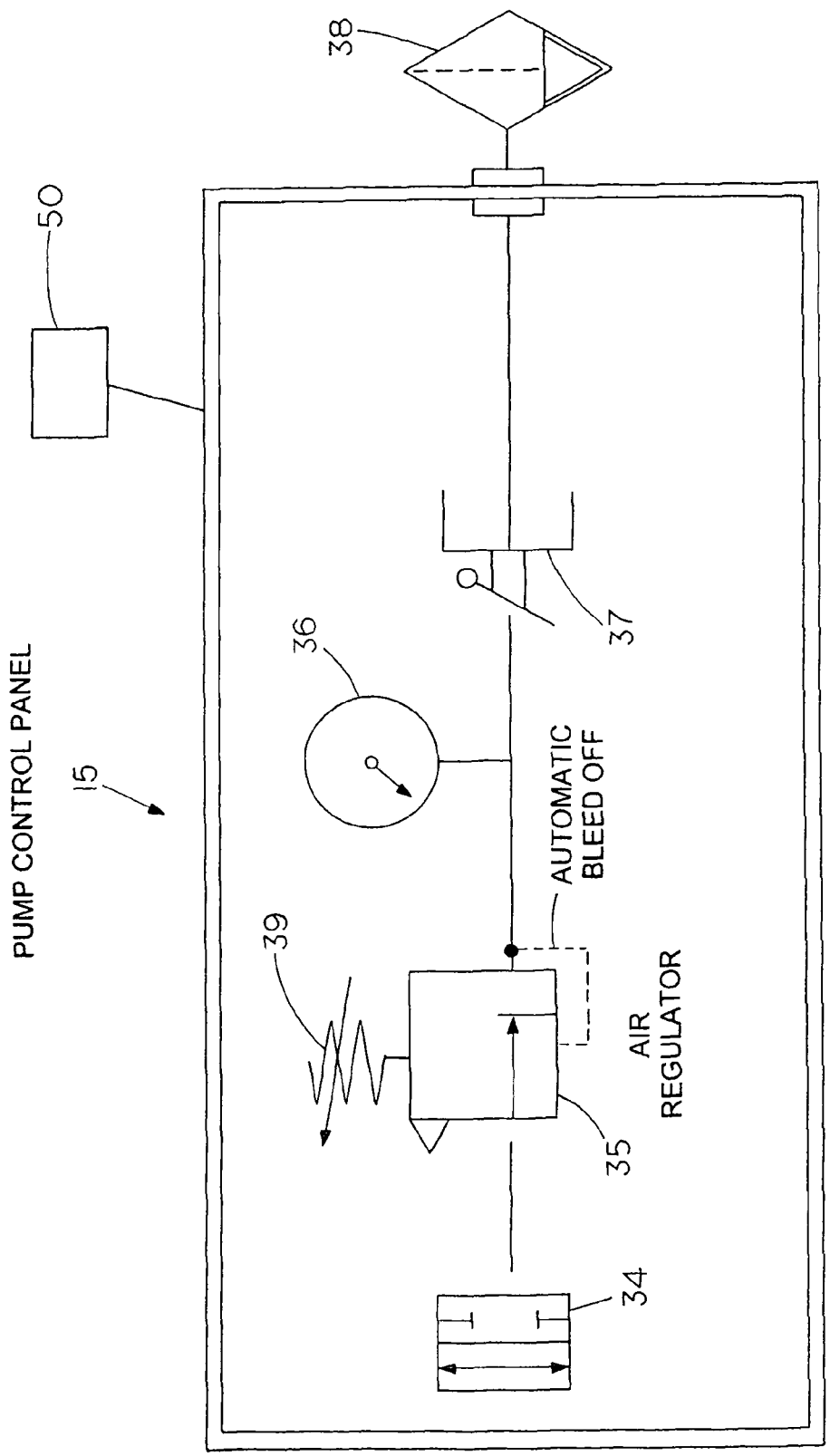
FIG. 4 is a schematic view showing the general components of the control panel.

FIG. 4 is a schematic view showing the general components of the control panel 16 of safety system 10 comprising a pump on/off switch 34, an air regulator 35, an air drive pressure gauge 36, a ball valve 37, and a filter 38. Pump on/off switch 34 functions by sending a pneumatic signal to the corresponding high-pressure equipment testing device to either turn on or off the particular device. Pump on/off switch 34 is shown in fluid communication with air regulator 35, which includes an adjustable resistor 39 to allow the user to control or set the amount fluid flow that is directed into control panel 16. To prevent over pressurization, air regulator 35 has the ability to automatically bleed off excess air that is directed through control panel 16.

Air regulator 35 is shown in fluid communication with ball valve 37, which functions to control the main pressure of control panel 15 on and off. Located between and in fluid communication with air regulator 35 and ball valve 37 is air drive pressure gauge 36, which similar to air drive pressure gauge 25, functions to display the pressure being directed through control panel 16. Also in fluid communication with ball valve 37 is filter 38, which functions to remove and automatically drain liquids from the air entering control panel 16. In the embodiment of FIG. 4, control panel 16 is shown also including means for monitoring and recording the operation of the high-pressure pneumatics testing equipment comprising a chart recorder.

Figure 5:
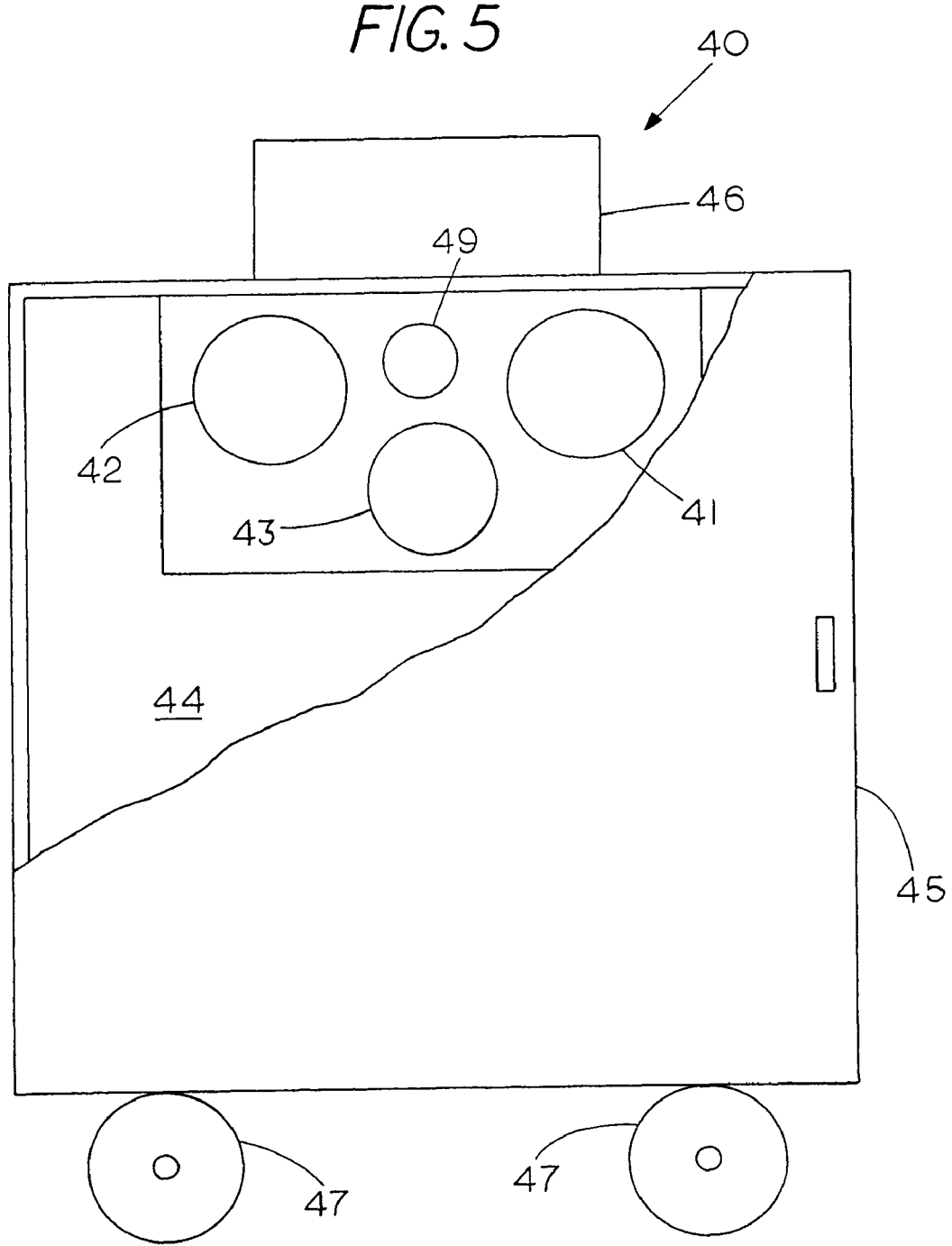
FIG. 5 shows a schematic view of an embodiment of a portable safety system.

FIG. 5 shows a schematic view of an embodiment of a portable safety system 40 of the present invention for safe pressure testing of high-pressure devices using various fluids including but not limited to air, nitrogen dioxide water and various types of oils. Portable safety system 40 comprise similar components to the safety system 10 of FIG. 1, namely a low-pressure pump 41, an intermediate-pressure pump 42, a high-pressure pump 49 and a bleed valve 43 and most if not all associated pumps, plumbing, hoses, and bleed valves located entirely within chamber 44 of a testing housing 45.

The low-pressure pump 41, intermediate-pressure pump 42, high-pressure pump 49 and bleed valve 43 are all linked to and controlled by a control panel 46 that is located outside of chamber 44. However, unlike the bunker housing 11 of safety system 10, which comprises a stationary enclosure, the testing housing 45 of portable safety system 40 comprises a smaller portable enclosure or housing that may be moved to different testing sites. For ease in transportation, the control panel 46 may be attached to an exterior surface of the test housing 45 and the housing may include wheels 47 to expedite the transport of portable safety system 40.

Although testing housing 45 may be form from a plurality of materials that is able to withstand the impact of high velocity projectile/high-speed flying fragments resulting from explosion of pressure equipments including valves, piping, fittings, ruptured disks, intensifiers and pumps, as well as pressure vessels, due to the portability of safety system 40, the materials that testing housing 45 is constructed from preferably comprises the property of being light in weight. One example of a suitable material is aluminum.

The present invention also includes a method for safely testing high-pressure devices comprising the steps of (1) providing an explosion-proof safety housing 11, 45; (2) placing high-pressure pneumatics testing equipment within the explosion-proof safety housing 11, 45; (3) forming a closeable access opening 19 in the explosion-proof safety housing 11, 45; (4) inserting a high-pressure device for testing within the explosion-proof safety housing 11, 45 through the access opening 19; (5) providing a control panel 16, 46 outside the explosion-proof safety housing 11, 45; (6) coupling the control panel 16, 46 to the testing equipment inside the explosion-proof safety housing 11, 45; and (7) then operating the high-pressure pneumatics testing equipment from the control panel 16, 46 for testing high-pressure devices.

The above method may further include the step of (8) providing a low-pressure pump 14, 41, an intermediate-pressure pump 13, 42, and a high-pressure pump 48, 49 within the explosion-proof safety housing 11, 45 to provide sequential increase in the pressure to the testing high-pressure devices; (9) monitoring and recording of the operation of the high-pressure pneumatics testing equipment from the control panel 16, 46; (10) providing a bleed valve 15, 43 coupled to the high-pressure testing equipment; and (11) providing a sensor 20 for sensing that the access opening 19 is closed with the sensor 20 coupled to the bleed valve 15, 43 to activate the bleed valve 15, 43 to prevent pressure buildup in the high-pressure testing equipment if the access opening is not closed; and (12) providing a bleed valve having a spring maintaining the bleed valve 15, 43 in an opened condition to prevent pressure build-up in the high-pressure pneumatics testing equipment and is air operated to actuate the bleed valve 15, 43 to a closed condition to allow pressure build-up in the high-pressure pneumatics testing equipment.

I claim:

1. A safety system for testing high-pressure devices comprising:
   an explosion-proof safety housing;
   a high-pressure pneumatics testing equipment located within said housing;
   a bleed valve coupled to said high-pressure pneumatics testing equipment;
   a closeable access opening in said housing for inserting a high-pressure device for testing within said housing;
   means within said housing for coupling said high-pressure pneumatics testing equipment to said high-pressure device for testing;
   a control panel located remote from said housing; and
   means linking said high-pressure pneumatics testing equipment to said control panel for operating said high-pressure pneumatics testing equipment within said safety housing from said control panel.

2. The safety system for testing high-pressure devices as described in claim 1 wherein said means linking said high-pressure pneumatics testing equipment to said control panel includes means for monitoring and recording the operation of said high-pressure pneumatics testing equipment.

3. The safety system for testing high-pressure devices as described in claim 1 further including:
   a sensor for sensing that said access opening is closed, said sensor coupled to said bleed valve to activate said bleed valve to prevent pressure buildup in the high-pressure testing equipment if the access opening is not closed.

4. The safety system for testing high-pressure devices as described in claim 3 wherein said sensor for sensing that said access opening is closed is located at said access opening.

5. The safety system for testing high-pressure devices as described in claim 3 wherein said bleed valve includes a spring maintaining said bleed valve in an opened condition to prevent pressure build-up in said high-pressure pneumatics testing equipment and is air operated to actuate said bleed valve to a closed condition to allow pressure build-up in said high-pressure pneumatics testing equipment.

6. The safety system for testing high-pressure devices as described in claim 1 wherein the high-pressure equipment testing device includes a low-pressure pump, an intermediate-pressure pump, and a high-pressure pump to provide sequential increase in the pressure to said high-pressure devices being tested.

7. The safety system for testing high-pressure devices as described in claim 1 wherein said explosion-proof safety housing comprises a stationary housing.

8. The safety system for testing high-pressure devices as described in claim 1 wherein said explosion-proof safety housing comprises a portable housing.

9. The safety system for testing high-pressure devices as described in claim 1 wherein said means linking said high-pressure testing equipment to said control panel comprises reinforced tubing.

10. The safety system for testing high-pressure devices as described in claim 1 wherein said system is pneumatically controlled.

11. A safety system for testing high-pressure devices comprising:
   an explosion-proof safety housing;
   high-pressure pneumatics testing equipment located within said housing;
   a closeable access opening in said housing for inserting a high-pressure device for testing within said housing;
   means within said housing for coupling said high-pressure pneumatics testing equipment to said high-pressure device for testing;
   a control panel located remote from said housing;
   a bleed valve coupled to said high-pressure testing equipment;
   a sensor for sensing that said access opening is closed, said sensor coupled to said bleed valve to activate said bleed valve to prevent pressure buildup in the high-pressure testing equipment if the access opening is not closed; and
   means linking said high-pressure pneumatics testing equipment to said control panel for operating said high-pressure pneumatics testing equipment within said safety housing from said control panel.

12. The safety system for testing high-pressure devices as described in claim 11 wherein said means linking said high-pressure pneumatics testing equipment to said control panel includes means for monitoring and recording of the operation of said high-pressure pneumatics testing equipment.

13. The safety system for testing high-pressure devices as described in claim 11 wherein said high-pressure equipment testing device includes a low-pressure pump, an intermediate-pressure pump, and a high-pressure pump to provide sequential increase in the pressure to said high-pressure devices being tested.

14. The safety system for testing high-pressure devices as described in claim 11 wherein said explosion-proof safety housing comprises a portable housing.

15. The safety system for testing high-pressure devices as described in claim 11 wherein said bleed valve includes a spring maintaining said bleed valve in an opened condition to prevent pressure build-up in said high-pressure pneumatics testing equipment and is air operated in opposition to said spring to actuate said bleed valve to a closed condition to allow pressure build-up in said high-pressure pneumatics testing equipment.

16. A method for safely testing high-pressure devices comprising the steps of:
   providing an explosion-proof safety housing;
   placing a low-pressure pump, an intermediate-pressure pump, and a high-pressure pump within said housing to provide sequential increase in the pressure to said testing high-pressure devices;
   forming a closeable access opening in said housing;
   inserting a high-pressure device for testing within said housing through said access opening;
   providing a control panel outside said housing;
   coupling said control panel to the testing equipment inside said housing; and then
   operating said high-pressure pneumatics testing equipment from said control panel for testing high-pressure devices.

17. The method for safely testing high-pressure devices as described in claim 16 including the step of monitoring and recording of the operation of said high-pressure pneumatics testing equipment from said control panel.

18. The method for safely testing high-pressure devices as described in claim 16 including the step of:
   providing a bleed valve coupled to said high-pressure testing equipment; and
   providing a sensor for sensing that said access opening is closed, said sensor coupled to said bleed valve to activate said bleed valve to prevent pressure buildup in the high-pressure testing equipment if the access opening is not closed.

19. The method for safely testing high-pressure devices as described in claim 18 wherein said bleed valve includes a spring maintaining said bleed valve in an opened condition to prevent pressure build-up in said high-pressure pneumatics testing equipment and is air operated to actuate said bleed valve to a closed condition to allow pressure build-up in said high-pressure pneumatics testing equipment.

* * * * *